(12) United States Patent
Bitensky et al.

(10) Patent No.: US 7,723,017 B2
(45) Date of Patent: May 25, 2010

(54) METHOD FOR EXTENDING THE USEFUL SHELF-LIFE OF REFRIGERATED RED BLOOD CELLS BY NUTRIENT SUPPLEMENTATION

(75) Inventors: Mark W Bitensky, Waban, MA (US); Tatsuro Yoshida, West Newton, MA (US)

(73) Assignee: The Trustees of Boston University, Boston, MA (US)

( * ) Notice: Subject to any disclaimer, the term of this patent is extended or adjusted under 35 U.S.C. 154(b) by 1 day.

(21) Appl. No.: 11/138,135

(22) Filed: May 26, 2005

(65) Prior Publication Data

US 2005/0277108 A1 Dec. 15, 2005

Related U.S. Application Data

(63) Continuation of application No. 10/295,772, filed on Nov. 15, 2002, now abandoned.

(60) Provisional application No. 60/332,409, filed on Nov. 16, 2001.

(51) Int. Cl.
*A01N 1/02* (2006.01)
(52) U.S. Cl. .......................................................... 435/2
(58) Field of Classification Search ........................ None
See application file for complete search history.

(56) References Cited

U.S. PATENT DOCUMENTS 5,624,794 A * 4/1997 Bitensky et al. ................ 435/2
5,789,151 A * 8/1998 Bitensky et al. ................ 435/2

FOREIGN PATENT DOCUMENTS

WO    WO 96/29864    * 10/1996

OTHER PUBLICATIONS

De Angelis et al., "Erythrocyte Shape Control in Stored Blood: The Effect of Additive Solutions on Shape Recovery", Haematologica 73: 7-12 (1988).*
Hamasaki et al., "Acid-citrate-dextrose-phosphoenolpyruvate medium as a rejuvenant for blood storage", Transfusion 23 (1) :1-7 (1983).*
Valeri et al., "The survival, function and hemolysis of human RBCs stored at 4C in additive solution . . . " Transfusion 40 :1341-4 (Nov. 2000).*

* cited by examiner

*Primary Examiner*—Sandra E Saucier
(74) *Attorney, Agent, or Firm*—Ohlandt, Greeley, Ruggiero & Perle, L.L.P

(57) ABSTRACT

There are provided methods and compositions for the storage of red blood cells. The compositions are metabolic supplements that are preferably added to refrigerated red blood cells suspended in an additive solution. Red blood cells are preferably stored under conditions of oxygen-depletion. Metabolic compositions comprises pyruvate, inosine, adenine, and optionally dibasic sodium phosphate and/or monobasic sodium phosphate.

8 Claims, 7 Drawing Sheets

METHOD FOR EXTENDING THE USEFUL SHELF-LIFE OF REFRIGERATED RED BLOOD CELLS BY NUTRIENT SUPPLEMENTATION

This application is a continuation application of U.S. patent Ser. No. 10/295,772, filed on Nov. 15, 2002, now abandoned. This application claims priority from U.S. Provisional Application No. 60/332,409, filed Nov. 16, 2001.

This invention was made with partial support by the United States Office of Naval Research, Contract No. N00014-98-1-0451. The Government has certain rights in the invention.

FIELD OF THE INVENTION

The present invention relates to the preservation of blood in liquid form. More particularly, the present invention relates to enhancement of the shelf-life of oxygen-depleted refrigerated storage of red blood cells. Still more particularly, compositions and methodology involving nutrient or metabolic supplementation of red blood cells stored in liquid form in oxygen-depleted refrigeration are provided.

DESCRIPTION OF THE PRIOR ART

By way of background, currently the supplies of liquid blood are limited by storage. Stored blood expires after about 42 days of refrigerated storage. Red blood cells may, for example, be stored under refrigeration at a temperature above freezing (4° C.) as packed blood cell preparations. Red blood cells may be concentrated from whole blood with separation of the liquid blood component (plasma). Expired blood cannot be used and is discarded. There are periodic shortages of blood that occur due to donation fluctuation, emergencies and other factors. The logistics of blood supply and distribution impact the military, especially during times of combat, and remote hospitals or medical facilities. There is currently a need for the storage of autologous blood to avoid the significant risks of infection associated with non-autologous donor blood. Patients currently cannot collect and store with current technology enough autologous blood for certain pre-planned surgeries, including hip replacement, organ transplantation and the like.

Storage of frozen blood is known in the art but such frozen blood has limitations. For a number of years, frozen blood has been used by blood banks and the military for certain high-demand and rare types of blood. However, frozen blood is difficult to handle. It must be thawed which makes it impractical for emergency situations. Once blood is thawed, it must be used within 24 hours.

U.S. Pat. No. 4,769,318 to Hamasaki et al. is directed to additive solutions for blood preservation and activation. U.S. Pat. No. 5,624,794 to Bitensky et al. and also U.S. Pat. No. 6,162,396 to Bitensky et al. are directed to the storage of red blood cells under oxygen-depleted conditions. U.S. Pat. No. 5,789,151 to Bitensky et al. is directed to blood storage additive solutions.

Additive solutions for blood preservation and activations are known in the art. For example, Rejuvesol (available from enCyte Corp., Braintree, Mass.) is add to blood after cold storage (i.e., 4° C.) just prior to transfusion or prior to freezing (i.e., at —80° C. with glycerol) for extended storage.

In light of current technology, there still remains a long-felt need for the extension of the useful shelf-life of stored liquid blood, especially for extension technology that is relatively inexpensive, easy to handle, and that provides significantly extended long-term storage.

Accordingly, it is an object of the present invention to provide a method for extended storage of red blood cells.

It is another object of the present invention to provide nutrient or metabolic supplements useful with the storage of red blood cells.

Another object of the present invention to provide a method for extending the storage of red blood cells using oxygen-free additive solutions and oxygen removal.

These and other objects and advantages of the present invention and equivalents thereof, are achieved by the methods and compositions of the present invention described herein and manifest in the appended claims.

SUMMARY OF THE INVENTION

The present invention provides methods and compositions for extending the useful shelf-life of red blood cells. The method of the invention comprises adding a metabolic supplement to packed red blood cells, adding an additive solution, preferably an oxygen-free additive solution, to said red blood cells, and storing said red blood cells at a temperature above freezing, preferably 4° C., under conditions of oxygen-depletion. Metabolic supplement compositions of the invention comprise pyruvate, inosine, adenine, monobasic and dibasic phosphate salts at a pH from about 5 to about 8. Rejuvesol, or modification thereof, may be used as a metabolic supplement solution. Oxygen depletion may be effected by flushing the red blood cells with an inert gas as described with oxygen depleted refrigerated storage in U.S. Pat. Nos. 5,624,794 and 6,162,396. Preferred oxygen-free additive solutions comprise modifications of EAS61 (Hess et al., Transfusion 40: 1007-1011), and OFAS1 (U.S. Pat. No. 5,789,151). A preferred oxygen-free additive solution is OFAS3. The present invention extends the useful shelf life of refrigerated packed red blood cells from the current approximately 6 week limit to about 12 to about 20 weeks.

DETAILED DESCRIPTION OF THE INVENTION

Figure 1:
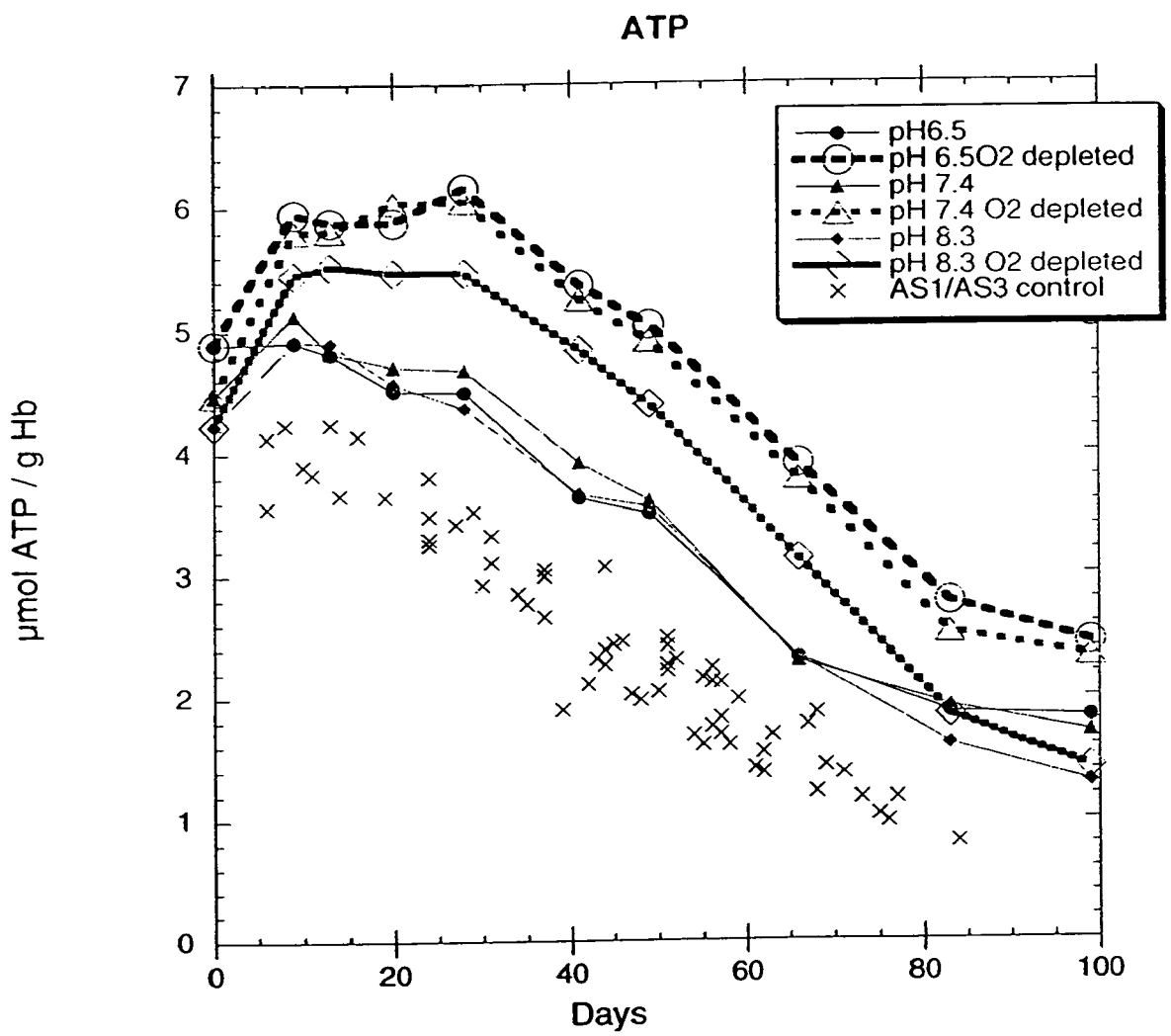
FIG. 1 shows the effect of pH and oxygen depletion on cellular ATP levels of red blood cells in OFAS3.

In its most general form, the present invention provides methods and compositions extending the useful shelf life of refrigerated red blood cells. The present invention more than doubles the useful shelf life of red blood cells and overcomes current limitations in the blood industry by providing longer and less perishable blood supplies.

Metabolic supplementation is used commercially. For example, Rejuvesol is indicated for use at 37° C. and a 1 hour rejuvenation of stored blood just prior to transfusion or just prior to freezing in glycerol. The present invention describes addition of metabolic supplement during refrigerated storage combined with the use of oxygen free additive solution (i.e., OFAS3) and oxygen removal. With this approach, unprecedented results have been obtained. For example, red blood cell storage well beyond the current 6-week limit for 12 or up to 20 weeks at 4° C. with levels of 2-3 DPG and ATP that are above those found in freshly drawn blood. A rationale for this efficacy is suggested or inferred from the fact that in the cold, earlier enzymatic steps of the glycolytic pathway are more seriously impaired than the later enzymatic steps. Thus, by bypassing the earlier enzymatic steps of glycolysis with the addition of metabolic intermediates that directly feed or serve as substrates for the later enzymatic steps, we have been able to significantly boost the production of ATP and 2-3 DPG. The fact that these substrates readily traverse the erythrocyte membrane at cold temperature (i.e., 4° C.) is clearly demonstrated by the experimental results obtained which are presented herein. The use of Rejuvesol in its current formulation does incur the need for a simple wash step prior to transfusion.

Metabolic supplementation of the invention is effected at least once, preferably during oxygen-depleted refrigerated storage (i.e., 4°) of red blood cells (c.f., U.S. Pat. Nos. 5,624, 794; 6,162,396), along with oxygen-free additive solution, preferably OFAS3 or modification thereof. Blood units are not warmed. EAS61 and OFAS1 are additive solutions known in the art.

Metabolic supplement is added to refrigerated red blood cells. A first addition is made within 6-10 weeks of storage. A second addition is optionally added within 11-20 weeks of storage.

Metabolic supplement solution composition is presented in Table 1.

TABLE 1

| Ingredient | Concentration (g/unit of addition) |
|---|---|
| Na pyruvate | 0.1-2.0 |
| Inosine | 0.5-3.0 |
| Adenine | 0.01-1.0 |
| Na phosphate dibasic | 0-2.0 |
| Na phosphate monobasic | 0-2.0 |
| pH | 5.5-8.0 |

The concentrations, given in mM units, of various blood additive solutions are presented in Table 2.

TABLE 2

| Ingredient | AS-3 | AS-1 | OFAS1 | EAS61 | OFAS3 |
|---|---|---|---|---|---|
| Adenine | 2.2 | 2 | 2 | 2 | 2 |
| Dextrose | 61 | 122 | 110 | 110 | 110 |
| Mannitol | — | 42 | 65 | 55 | 55 |
| NaCl | 70 | 154 | — | 26 | 26 |
| Na citrate | 20 | — | 20 | — | — |
| Citric acid | 2 | — | — | — | — |
| $Na_2HPO_4$ | — | — | — | 12 | 12 |
| $NaH_2PO_4$ | 20 | — | 20 | — | — |
| pH | | | 7.2* | 8.3 | 6.5* |
| vol. added (mL) | 200 | | 250 | 200 | 200 |
| final Hct | ~40 | | ~35 | ~40 | ~10 |

*pH adjusted with NaOH

Preferred concentration ranges of OFAS3 are presented in Table 3.

TABLE 3

| Ingredient | Range (mM) |
|---|---|
| Adenine | 0.5-4.0 |
| Dextrose | 50-150 |
| Mannitol | 20-70 |
| NaCl | 0-100 |
| $NaH_2PO_4$ | 2-20 |
| $NH_4Cl$ | 0-30 |
| pH | 5.5-7.7 |
| mL added | 100-300 |
| Final Hct | 30-50 |

The following Examples are illustrative of the invention and are not intended to be limitative thereof.

EXAMPLE 1

OFAS3: Effect of pH and Oxygen Depletion on Cellular ATP Levels

Results of experimentation to determine the effect of pH and oxygen depletion on cellular ATP levels with blood samples containing oxygen-free additive solution (OFAS3) are presented in FIG. 1. Each point on the graph is the average of 6 subjects. For comparative purposes, AS1 and AS3, the current U.S. standard additive solution, serve as a control. There is a large variability in the values between different test subjects. In order to see the effect of pH, P values (t-test for paired two samples for means) were calculated and are presented in Table 4.

TABLE 4

| Pairwise Test of ATP Values (For Oxygen Depleted Storage at Various pH's) | | |
|---|---|---|
| Time (Days) | $P(T <= t)$ one-tail pH 6.5 vs. pH 8.3 | $P(T <= t)$ one-tail pH 6.5 vs. pH 7.4 |
| 9 | 0.002 | 0.007 |
| 13 | 0.032 | 0.327 |
| 20 | 0.008 | 0.116 |
| 28 | 0.001 | 0.104 |
| 41 | 0.072 | 0.072 |
| 49 | 0.023 | 0.111 |
| 66 | 0.008 | 0.149 |
| 83 | 0.007 | 0.147 |
| 99 | 0.008 | 0.388 |

Although there are large subject to subject variations in ATP levels, there are significant differences between pH 6.5 and pH 8.3. These data show that oxygen depletion further enhances ATP levels as much as 33% by week 3 and 38% by week 14. The increase in ATP levels is dramatically enhanced when red blood cells are stored in oxygen depleted conditions. The best result was obtained with additive solution (OFAS3) at pH 6.5 with oxygen depletion.

EXAMPLE 2

Figure 2:
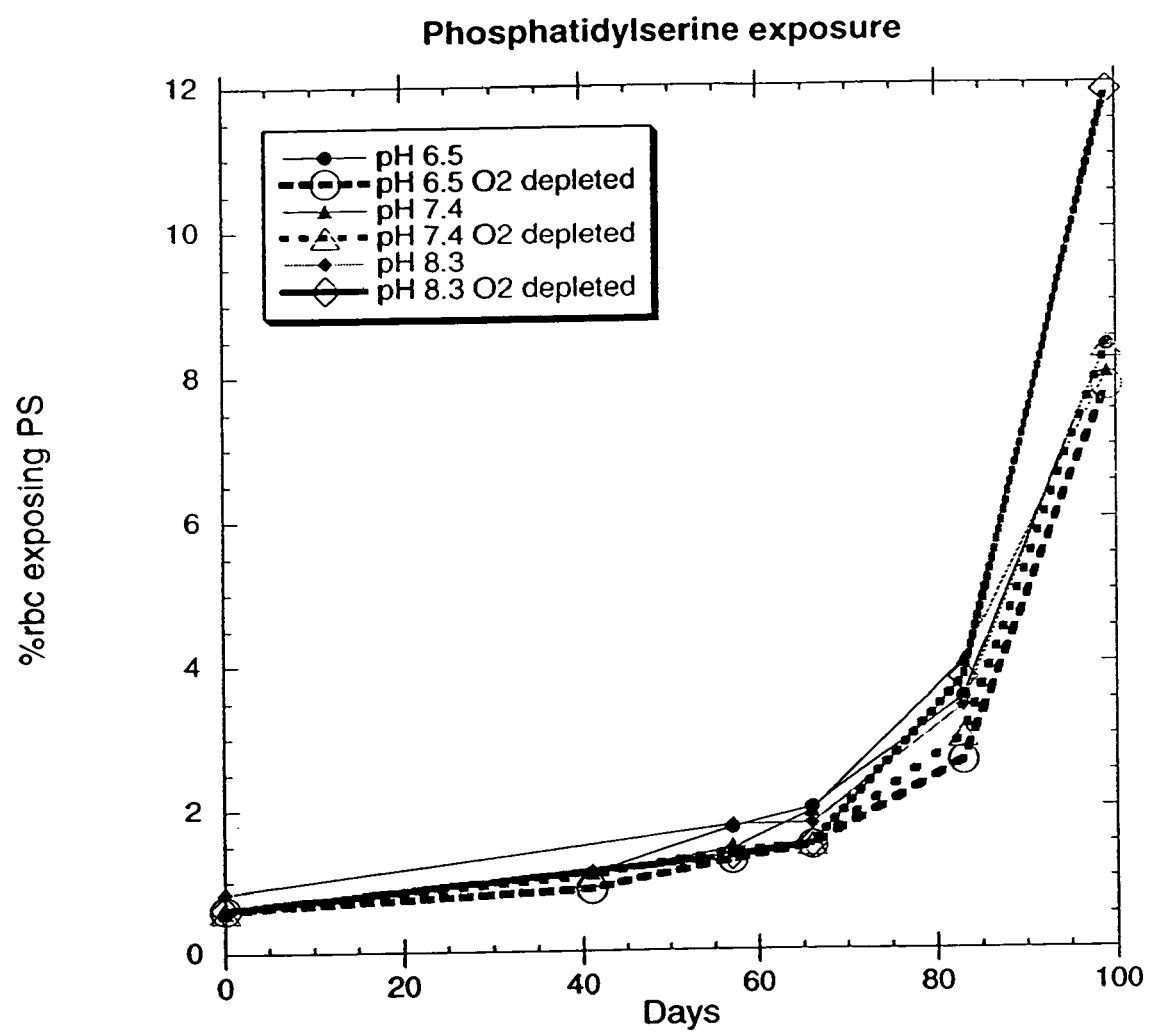
FIG. 2 shows the effect of pH and oxygen depletion on the percentage of red blood cells exposing phosphotidylserine in OFAS3.

OFAS3: Effect of pH and Oxygen Depletion on % of Cells Exposing Phosphotidylserine Results of experimentation to determine the effect of pH and oxygen depletion on the % of red blood cells exposing phosphotidylserine with samples containing oxygen-free additive solution (OFAS3) are presented in FIG. 2. Data were obtained by flow cytometer measurements using FITC-Annexin IV probe. Each point on the graph is the average of 6 subjects. There is a significant reduction in exposed phosphotidylserine after 10 weeks when pH 8.3 and pH 6.5 blood samples, both oxygen depleted, are compared.

EXAMPLE 3

OFAS3: Effect of pH and Oxygen Depletion on Red Blood Cell Hemolysis

Figure 3:
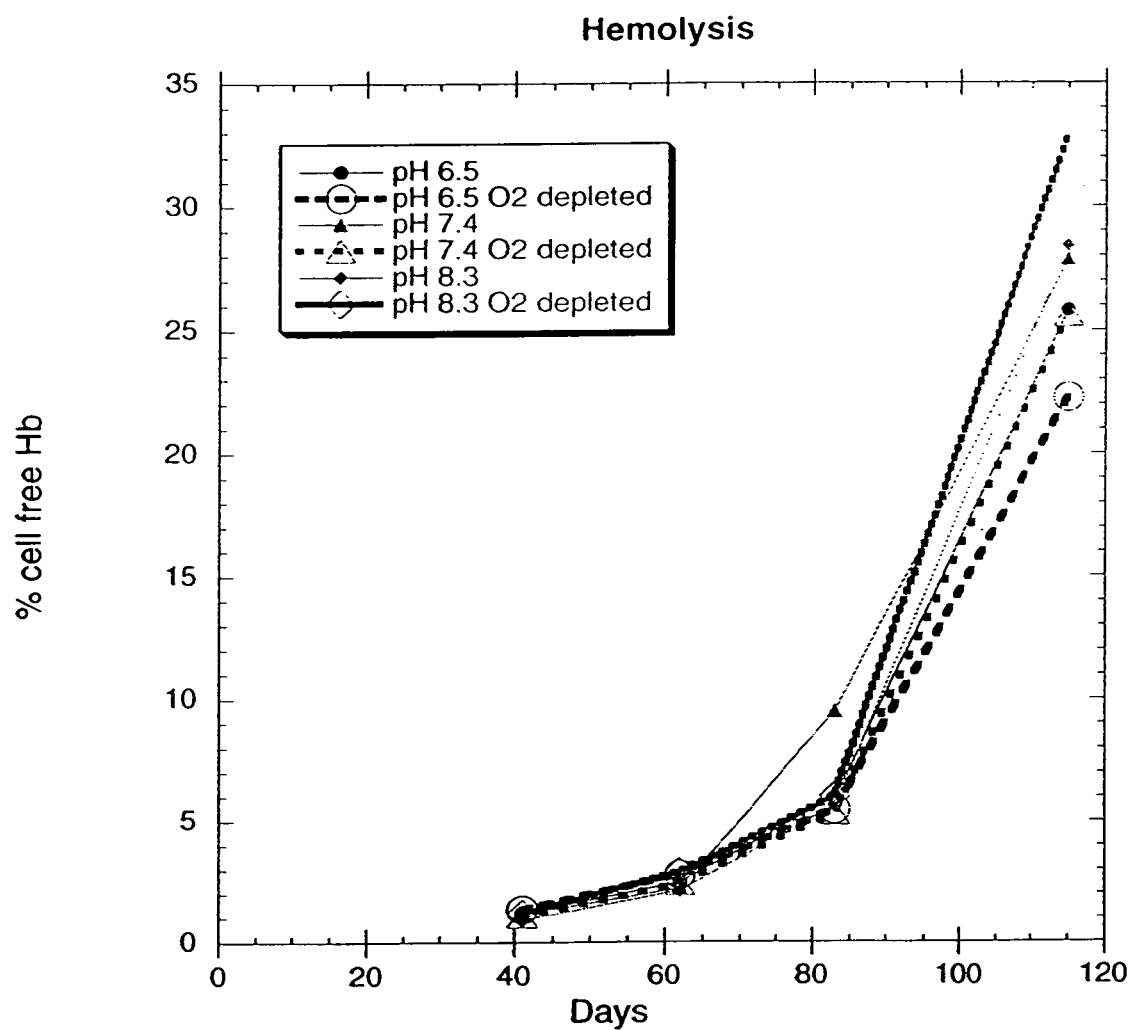
FIG. 3 shows the effect of pH and oxygen depletion on red blood cell hemolysis in OFAS3.

Results of experimentation to determine the effect of pH and oxygen depletion on red blood cell hemolysis with blood samples containing oxygen-free additive solution (OFAS3) are presented in FIG. 3. Each point on the graph is the average of 6 subjects. Three different pH's were tested, pH 6.5, pH 7.4, and pH 8.3, with control cultures that were not oxygen-depleted. At week 16, the pH 6.5 oxygen-depleted refrigerated red blood cell storage system has the lowest extent of hemolysis.

EXAMPLE 4

Figure 4:
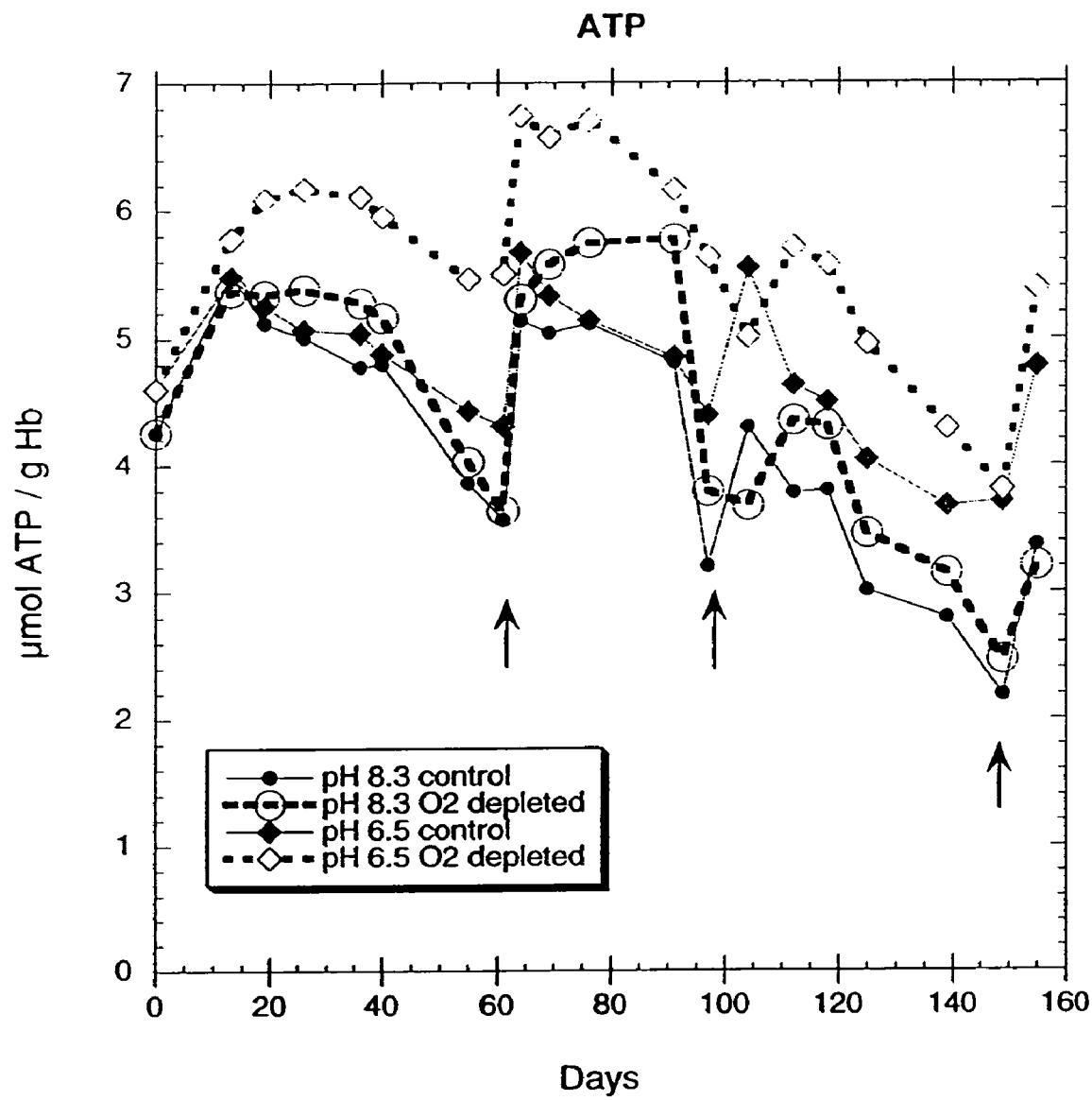
FIG. 4 shows the effect on red blood cell ATP levels of metabolic supplements added at different pH's in the presence or absence of oxygen.

Addition of Metabolic Supplements During Refrigerated, Oxygen-Depleted Red Blood Cell Storage: Effect of Metabolic Supplements Added at Different pH's in the Presence or Absence of Oxygen on Cellular ATP Levels Results of experimentation to determine the effect of addition of metabolic supplements added during refrigerated, oxygen-depleted storage of red blood cells at different pH's in the presence or absence of oxygen on cellular ATP levels, are graphically presented in FIG. 4. Two different pH's were tested, pH 6.5 and pH 8.3, with control cultures that are not oxygen depleted. Metabolic supplement, Rejuvesol, was added to cultures as indicated by the arrows in FIG. 4, which correspond approximately to additions during cold storage at 9, 14, and 21 weeks respectively. These data show that ATP levels are significantly increased each time the cold fuel/metabolic supplement is added. The highest ATP levels are sustained with pH 6.5 additive solution under oxygen depleted conditions. ATP levels are sustained near or above day 0 values throughout 22 weeks of storage with the additions of cold fuel.

EXAMPLE 5

Figure 5:
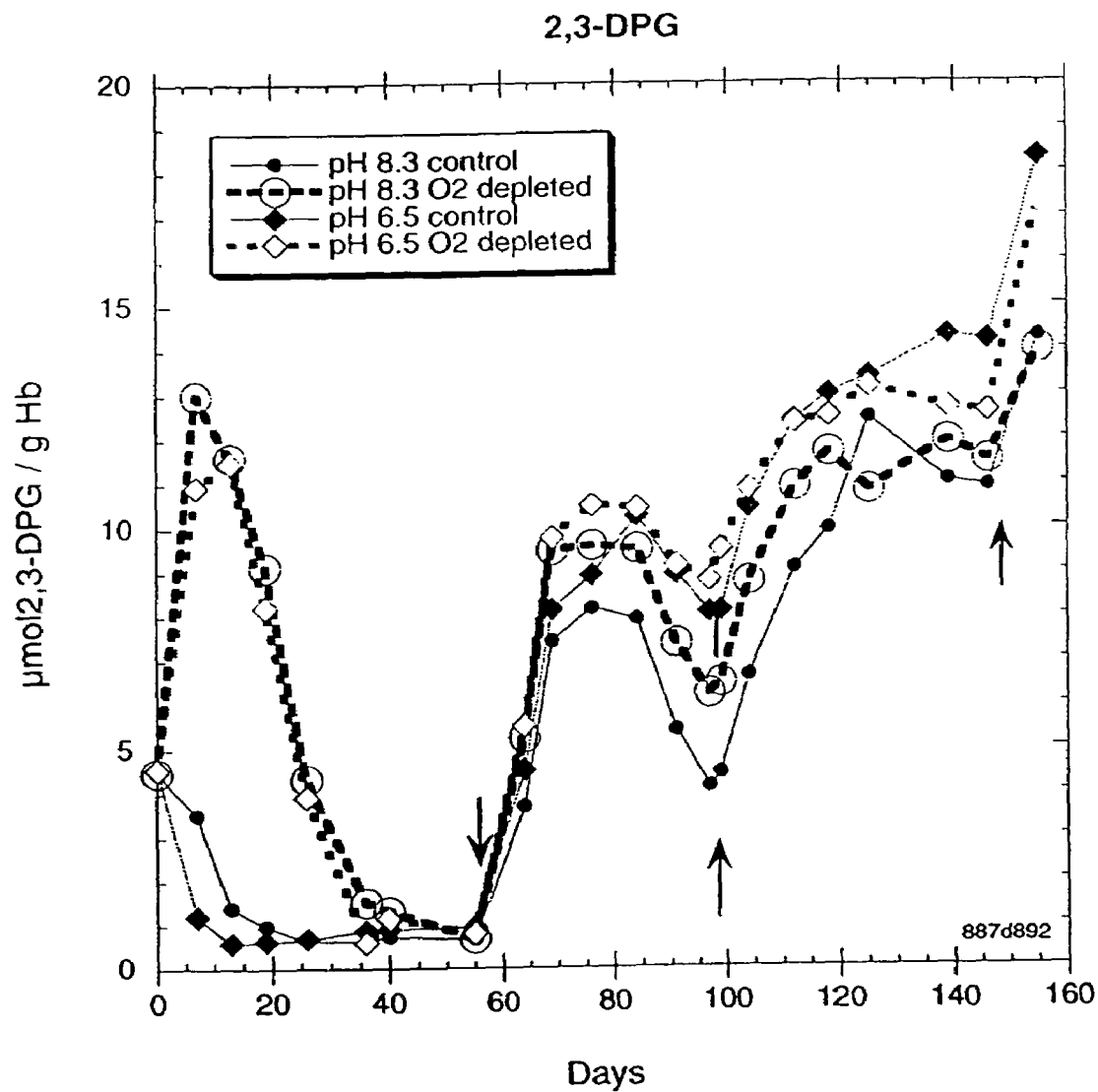
FIG. 5 shows the effect on red blood cell 2,3-DPG levels of metabolic supplements added at different pH's in the presence or absence of oxygen.

Addition of Metabolic Supplements During Refrigerated Oxygen-Depleted Red Blood Cell Storage: Effect of Metabolic Supplements Addition at different pH's in the Presence and Absence of Oxygen on Cellular 2,3-DPG Levels Results of experimentation to determine the effect of addition of metabolic supplements during refrigerated, oxygen-depleted red blood cell storage in the presence or absence of oxygen on cellular 2,3-DPG levels, are presented in FIG. 5. Each point on the graph is the average of 6 subjects. Two different pH's were evaluated, pH 6.5 and pH 8.3. Control cultures are not oxygen-depleted. Metabolic supplement, Rejuvesol, was added at the time indicated by the arrows, which correspond approximately to 8, 14, and 20 weeks respectively. These data show that oxygen depletion elevates 2,3-DPG levels significantly at the start of storage, without addition of metabolic supplements. Addition of metabolic supplements increases 2.3-DPG levels slowly at 4° C., and keeps these levels well above day 0 values, thus enhancing oxygen delivery capacity of the transfused blood.

EXAMPLE 6

Figure 6:
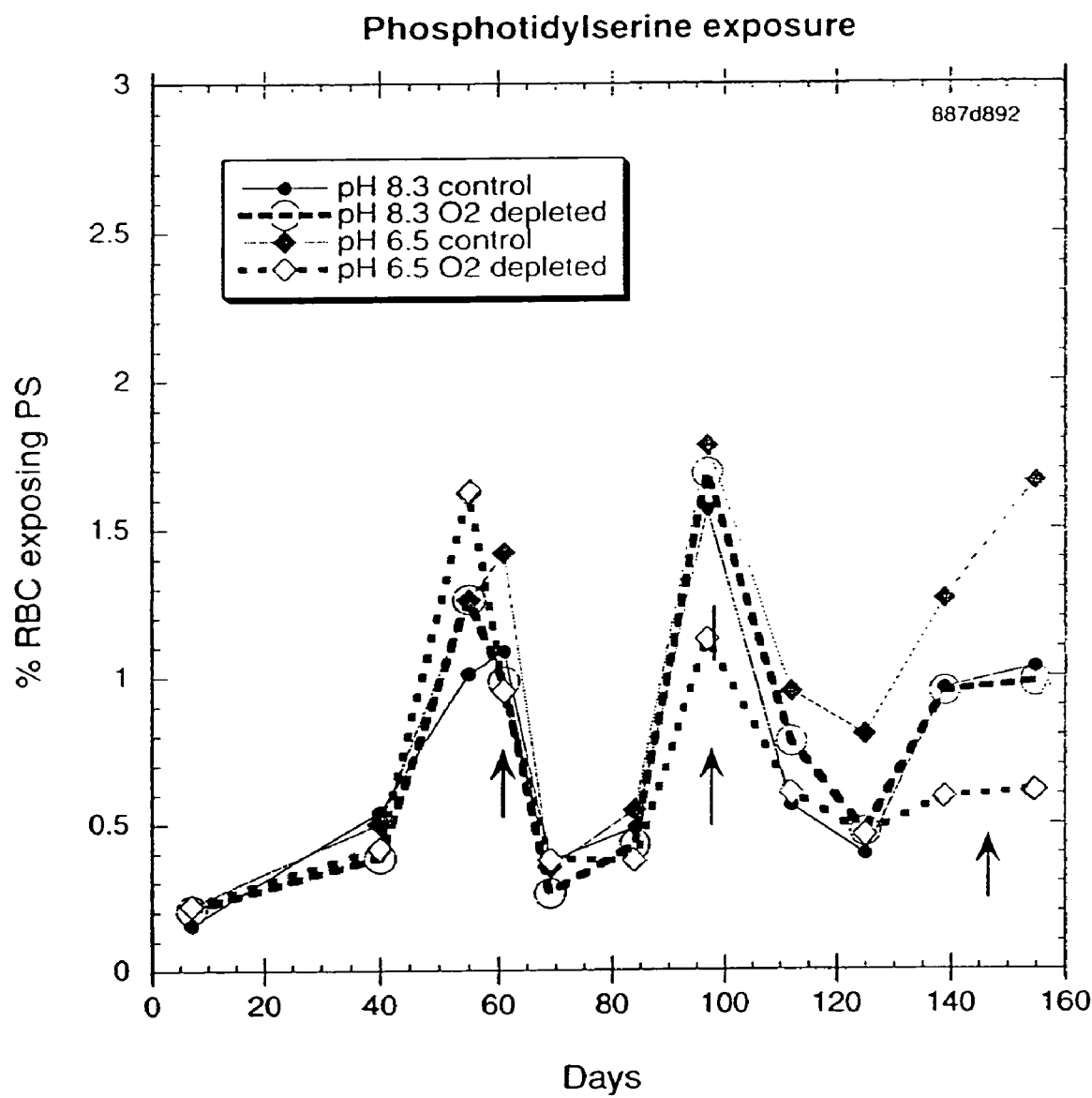
FIG. 6 shows the effect on the percentage of red blood cells exposing phosphotidylserine of addition of metabolic supplements at different pH's in the presence and absence of oxygen.

Addition of Metabolic Supplements During Refrigerated Oxygen-Depleted Red Blood Cell Storage: Effect of Metabolic Supplements Addition at different pH's in the Presence and Absence of Oxygen on the % of Red Blood Cells Exposing Phosphotidylserine Results of experimentation to determine the effect of addition of metabolic supplements during refrigerated, oxygen-depleted red blood cell storage in the presence or absence of oxygen on the percent of red blood cells exposing phosphotidylserine are presented in FIG. 6. Data were obtained from measurements by flow cytometer using FITC-Annexin IV probe. Each point on the graph represents the average of 6 subjects. Two different pH's were evaluated, pH 6.5 and pH 8.3, with metabolic supplement, Rejuvesol, added at the time indicted by the arrows which correspond to additions at approximately 8.6, 14, and 20 weeks. Control cultures are not oxygen-depleted. Phosphotidylserine is gradually exposed during refrigerated (4° C.). However, addition of metabolic supplements reverses this exposure. This experiment has been repeated three times with similar results. The lowest levels of exposure were seen with pH 6.5 storage buffer with oxygen depletion.

EXAMPLE 7

Figure 7:
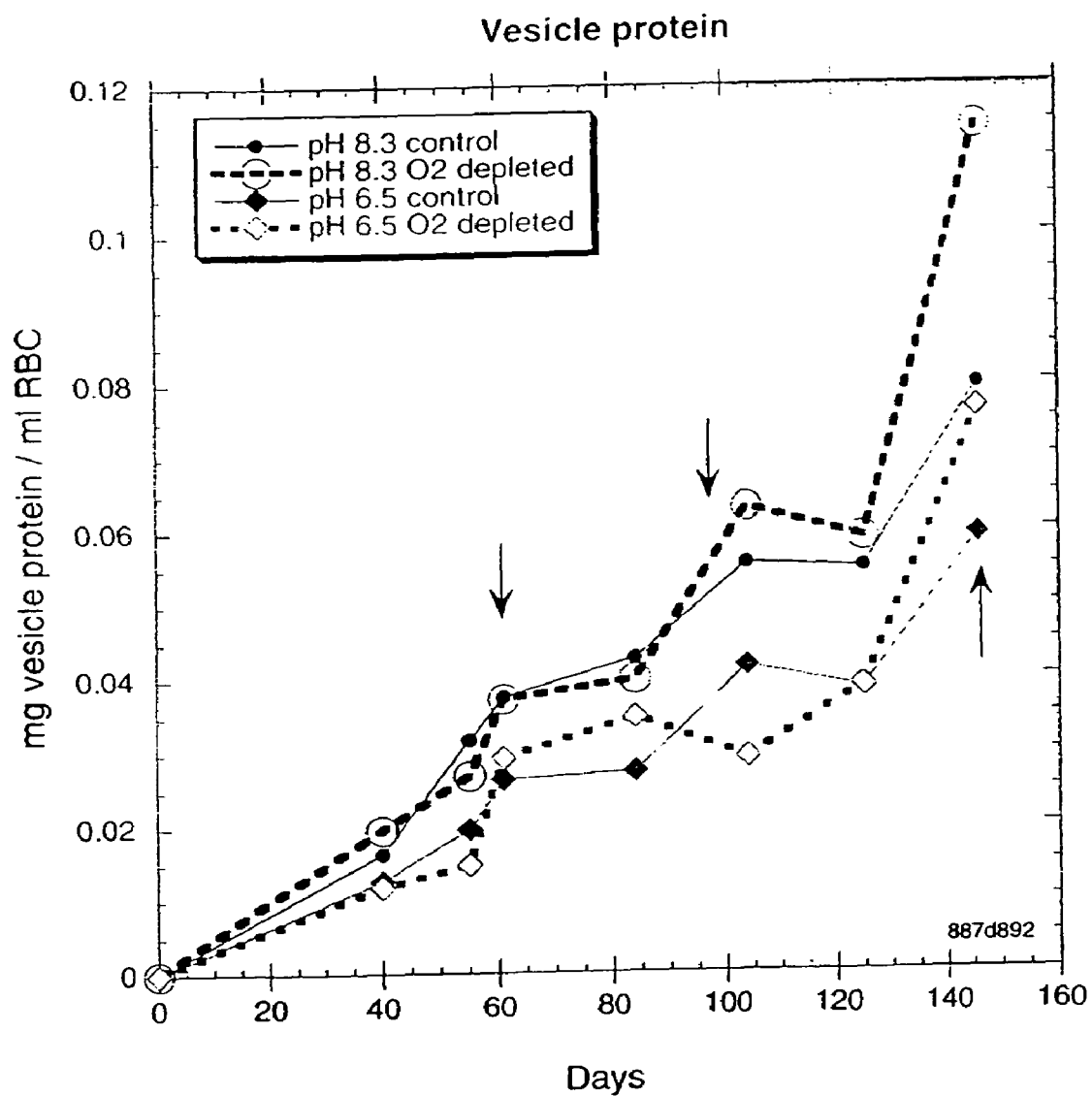
FIG. 7 shows the effect on vesicle protein production of red blood cells of addition of metabolic supplements at different pH's in the presence or absence of oxygen.

Addition of Metabolic Supplements During Refrigerated Oxygen-Depleted Red Blood Cell Storage: Effect of Metabolic Supplements Addition at different pH's in the Presence and Absence of Oxygen on Vesicle Production Results of experimentation to determine the effect of addition of metabolic supplements during refrigerated, oxygen-depleted red blood cell storage in the presence or absence of oxygen on the vesicle production are presented in FIG. 7. Each point on the graph represents the average of 6 subjects. Two different pH's were evaluated, pH 6.5 and pH 8.3, with metabolic supplement, Rejuvesol, added at the time indicted by the arrows which correspond to additions at approximately 8.6, 14, and 20 weeks respectively. Control cultures are not oxygen-depleted. It is known that refrigerated red blood cells shed vesicles during storage. Addition of metabolic supplements slows vesicle production. In the system comprising metabolic supplementation during oxygen-depleted refrigerated storage with oxygen-free additive solution, the additive solution OFAS3 was shown to be the most effective of such additives.

EXAMPLE 8

Twenty-Four-Hour In Vivo Post Transfusion Survival of Stored Red Cell Units

Eight normal subjects each donated a unit of whole blood via a standard, manual method on two separate occasions approximately 8 weeks apart. Subject requirements were the same as those that apply for allogeneic blood donors as established by 21 CFR640.3 and the Standards of the American Association of Blood Banks. These units were processed via centrifugation to yield packed red cells via a "soft spin" technique (2000 g *3 min) following holding at room temperature for 1-2 hours, and 200 mL of an experimental additive solution OFAS3 were added (Table 2) to yield a final hematocrit of 35-45%. These and all other manipulations of units involving addition of solutions or sampling were accomplished via a sterile connection device.

The test units were stored in an anaerobic environment following multiple flushes to minimize the oxygen content of each unit using highly purified Ar and $H_2$ Following completion of sampling, the test units were made anaerobic following the procedure provided by the sponsor. Briefly, the units were transferred to a 2000 mL transfer bag using the SCD. Sputtering grade argon was introduced into the unit via a 0.22 micron filter until the transfer bag was completely filled with gas/blood and rotated 10 min at room temperature. Following this hold period, the gas was expelled through the same 0.22 micron filter using a plasma expressor and a vacuum line. This procedure was repeated 6 times, and the unit was transferred to a standard PL146 red cell storage bag with an Ar flush. The unit was then placed in an anaerobic culture jar and 3 exchanges of the contents of the jar were performed with Ar, the last consisting of 2 parts Ar, 1 part scientific grade $H_2$ before the jar was placed in a monitored 4° C. refrigerator. When subsequent samples were taken via the SCD, the storage jar again underwent gas replacement prior to the unit being placed back in the refrigerator. Jars were flushed weekly with Ar if no sampling occurred in that week. Control units were stored in the same refrigerator without altering their gaseous environment.

After 7 weeks of storage, test units underwent a metabolic supplementation using a licensed solution (Rejuvesol, Cytosol Laboratories, Braintree, Mass.); test units underwent an additional metabolic supplementation at 11 weeks (if recoveries to date indicated that continued storage was warranted, vida infra) The contents of the bottle of metabolic supplement were aspirated via needle and syringe and injected via a sampling port into a plastic transfer bag that had been previously flushed with Ar and to which had already been attached a 0.22 micron filter. The solution was then transferred to the unit by sterile docking, and the unit was promptly returned to refrigerated storage (without repeating the gas exchange procedure and without incubation or washing).

Control units were utilized for radiolabeling and autologous reinfusion at 10 weeks; test units were continued in the protocol so long as the prior radiolabeled recovery suggested the continued viability of the cells. In addition, for a radiolabeled recovery to be conducted, the ATP must have been at least 50% of the Day 0 value, and the hemolysis must have been no more than 3.0% at the preceding sampling.

Radiolabeling to allow for determination or in vivo red cell recovery' was conducted according to published procedures [J. Nucl. Med. 1975; 16:435-7] 10-20 µCi $Na_2^{51}CrO_4$ (Bracco, Princeton, N.J.) were added to a 10 mL aliquot of the unit's cells for 30 min. at room temperature followed by a single double-volume saline wash.[Blood 1871; 38:378-86; Transfusion 1984; 24:109-14] (Prior to labeling, cells from test units were washed four times with a double volume saline wash to remove remaining constituents of the rejuvenation solution.) These cells were injected simultaneously with fresh autologous red cells that had been labeled with 10-20 µCi $^{99m}$Tc pertechnetate after 'tinning"to determine the subject's red cell volume; [Dave, R. J., Wallacae, M. e., eds. Diagnostic and investigational uses of radiolabeled blood elements. Arlington: American Association of Blood Banks, 1987] labeled cells were washed once with 40 mL ice-cold saline. Reinfusions were conducted promptly after labeling, and labeled cells were kept on ice until then, Samples were taken from 5 to 30 min. and then at 24 h to determine circulating radioactivity. Red cell volumes were determined by single and double label calculation methods after correction for counting interference and $^{99m}$Tc label elution prior to injection Results of a 24-hr in vivo post tranfusion survival study of stored red cell units are presented in Table 5. Hemolysis remained below 1% through 14 weeks of storage. The maximum noted was 1.75% at 16 weeks in one unit.

TABLE 5

| | volunteer | | | | | | | | | |
|---|---|---|---|---|---|---|---|---|---|---|
| | A | B | C | D | E | F | G | n | Average | std dev |
| single label | | | | | | | | | | |
| 10 wks test | 73.9 | 74.2 | 69.6 | 72.5 | 64.6 | 81.9 | 90.3 | 7 | 75.3 | 8.4 |
| 12 wks test | 69.9 | 66.9 | 71.6 | 74.3 | | 78.05 | 84.6 | 6 | 74.2 | 6.3 |
| 14 wks test | 65.6 | 61.7 | 58.3 | 79.6 | | 74.2 | 78.8 | 6 | 69.7 | 9.1 |
| 16 wks test | | | | | | 69.7 | 75.1 | 2 | 72.4 | 3.8 |
| 10 wks control | 71.7 | 78.5 | 66.6 | 56.8 | 77.6 | 73.8 | 78.0 | 7 | 71.9 | 7.9 |
| double label | | | | | | | | | | |
| 10 wks test | 82.6 | 83.5 | 76.7 | 78.6 | 62.1 | 82.0 | 96.0 | 7 | 80.2 | 10.1 |
| 12 wks test | 67.1 | 68.3 | 78.4 | 75.0 | | 80.8 | 86.0 | 6 | 75.9 | 7.3 |
| 14 wks test | 64.8 | 63.6 | 57.1 | 78.7 | | 79.6 | 76.0 | 6 | 70.0 | 9.4 |
| 16 wks test | | | | | | 79.2 | 74.2 | 2 | 76.7 | 3.5 |
| 10 wks control | 72.4 | 79.7 | 68.2 | 49.7 | 74.5 | 69.7 | 73.7 | 7 | 69.7 | 9.6 |

Note:
12-week data for subjects F and G are linearly extrapolated from 10 and 14 week data
Test units: Packed red cells were stored under oxygen depleted conditions at 4 C. in OFAS3 storage solution. At weeks 7 and 11, metabolic supplements were added at 4 C.
Control units: Packed red cells were stored in OFAS3 storage solution at 4 C. without oxygen depletion or metablic supplement additions.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. A method for the storage of packed red blood cells comprising:

adding an additive solution selected from the group consisting of AS-3, EAS61, OFAS1, OFAS3, and mixture thereof, wherein OFAS3 comprises the following concentrations of adenine having a range of from 0.5-4.0 mM, dextrose having a range of from 50-150 mM, mannitol having a range of from 20-70 mM, NaCl having a range of from 0-100 mM, NaH2PO4 having a range of from 2-20 mM, NH4Cl having a range of from 0-30 mM, pH having a range of 5.5-7.7 and mL added having range of from 100-300 mL, to said red blood cells, thereby forming a suspension of red blood cells; and storing said suspension of red blood cells under oxygen depleted storage;

adding a metabolic supplement comprising pyruvate, inosine, adenine and optionally dibasic sodium phosphate and/or monobasic sodium phosphate at least once to said suspension of red blood cells, wherein said suspension of red blood cells are stored under refrigeration during said addition.

2. A method according to claim 1, wherein said red blood cells are packed red blood cells or suspended red blood cells in an additive solution.

3. A method according to claim 2, further comprising mixing whole blood with an anticoagulant solution, concentrating the whole blood cells from said whole blood and separating the plasma thereby creating a mass of packed red blood cells.

4. The method of claim 2, wherein said additive solution is an oxygen-free additive solution.

5. The method of claim 1, wherein said red blood cells are stored at 4° C.

6. A method for extending the storage life of refrigerated red blood cells comprising:

adding an additive solution selected from the group consisting of AS-3, EAS61, OFAS1, and OFAS3, wherein OFAS3 comprises the following concentrations of adenine having a range of from 0.5-4.0 mM, dextrose having a range of from 50-150 mM, mannitol having a range of from 20-70 mM, NaCl having a range of from 0-100 mM, NaH2PO4 having a range of from 2-20 mM, NH4Cl having a range of from 0-30 mM, pH having a range of 5.5-7.7 and mL added having range of from 100-300 mL to red blood cells;

storing said red blood cells under oxygen-depleted refrigeration; and adding a metabolic supplement comprising pyruvate, inosine, adenine and optionally dibasic sodium phosphate and/or monobasic sodium phosphate at least once to said red blood cells during refrigeration.

7. The method of claim 6, wherein said red blood cells are continuously stored at 4° C.

8. The method of claim 1 or claim 6, wherein said metabolic supplement is added at least a plurality of times during storage of said red blood cells.

* * * * *